(12) United States Patent
Collins et al.

(10) Patent No.: US 9,706,674 B2
(45) Date of Patent: Jul. 11, 2017

(54) AUTHENTICATION SYSTEM FOR REUSABLE SURGICAL INSTRUMENTS

(71) Applicant: Covidien LP, Mansfield, MA (US)

(72) Inventors: Ethan Collins, Naugatuck, CT (US); Paul Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 756 days.

(21) Appl. No.: 14/172,109

(22) Filed: Feb. 4, 2014

(65) Prior Publication Data

US 2015/0216525 A1    Aug. 6, 2015

(51) Int. Cl.
| | |
|---|---|
| *H05K 7/06* | (2006.01) |
| *A61B 17/072* | (2006.01) |
| *A61B 90/90* | (2016.01) |
| *A61B 90/98* | (2016.01) |
| *A61B 17/00* | (2006.01) |
| *A61B 90/00* | (2016.01) |

(52) U.S. Cl.
CPC ......... *H05K 7/06* (2013.01); *A61B 17/07207* (2013.01); *A61B 90/90* (2016.02); *A61B 90/98* (2016.02); *A61B 2017/0046* (2013.01); *A61B 2017/00473* (2013.01); *A61B 2017/00482* (2013.01); *A61B 2090/0803* (2016.02); *A61B 2090/0806* (2016.02); *A61B 2090/0808* (2016.02)

(58) Field of Classification Search
CPC .......... H05K 7/06; A61B 90/90; A61B 90/98; A61B 17/07207; A61B 2090/0803; A61B 2090/0808; A61B 2090/0806; A61B 2017/00482; A61B 2017/0046; A61B 2017/00473
See application file for complete search history.

(56) References Cited

U.S. PATENT DOCUMENTS

| | | | | |
|---|---|---|---|---|
| 2,588,006 | A | * | 3/1952 | Hufnagel ................. A61C 3/08 173/117 |
| D286,442 | S | | 10/1986 | Korthoff et al. |
| 4,731,058 | A | | 3/1988 | Doan |
| 5,391,166 | A | * | 2/1995 | Eggers ............... A61B 18/1206 606/170 |
| 5,529,235 | A | * | 6/1996 | Boiarski .......... A61B 17/07207 227/175.1 |

(Continued)

FOREIGN PATENT DOCUMENTS

| | | |
|---|---|---|
| EP | 0584838 | 5/1997 |
| FR | 2 849 589 | 7/2004 |

(Continued)

OTHER PUBLICATIONS

U.S. Appl. No. 13/715,364, filed Dec. 14, 2012, Aranyi.

(Continued)

*Primary Examiner* — Hemant M Desai
*Assistant Examiner* — Mobeen Ahmed (57) ABSTRACT

An authentication system for use in a surgical stapling device includes an authentication board assembly disposed at a proximal end of a loading unit and having a contact assembly, and an adapter board assembly disposed at a distal end of an adapter assembly. When the loading unit is engaged with the adapter assembly, the authentication board engages the adapter board assembly.

17 Claims, 10 Drawing Sheets

(56) References Cited

U.S. PATENT DOCUMENTS

| | | | |
|---|---|---|---|
| 6,533,157 B1* | 3/2003 | Whitman | A61B 17/0684 227/175.1 |
| 6,793,652 B1* | 9/2004 | Whitman | A61B 10/0233 128/898 |
| 6,997,751 B2 | 2/2006 | Miyamoto | |
| 7,721,931 B2 | 5/2010 | Shelton, IV et al. | |
| 7,887,530 B2 | 2/2011 | Zemlok et al. | |
| 8,397,971 B2 | 3/2013 | Yates et al. | |
| 2001/0031975 A1* | 10/2001 | Whitman | A61B 10/0233 606/167 |
| 2004/0220602 A1* | 11/2004 | Deng | A61B 17/32002 606/170 |
| 2004/0267297 A1* | 12/2004 | Malackowski | A61B 34/20 606/167 |
| 2006/0095096 A1* | 5/2006 | DeBenedictis | A61B 18/203 607/88 |
| 2008/0164296 A1* | 7/2008 | Shelton | A61B 17/07207 227/175.1 |
| 2008/0185419 A1* | 8/2008 | Smith | A61B 17/115 227/179.1 |
| 2009/0090763 A1* | 4/2009 | Zemlok | A61B 17/07207 227/175.2 |
| 2010/0294829 A1* | 11/2010 | Giordano | A61B 17/00 227/176.1 |
| 2011/0155784 A1* | 6/2011 | Shelton, IV | A61B 17/07207 227/176.1 |
| 2011/0290855 A1* | 12/2011 | Moore | A61B 17/072 227/180.1 |
| 2011/0297731 A1* | 12/2011 | Aranyi | A61B 17/07207 227/176.1 |
| 2012/0116388 A1* | 5/2012 | Houser | A61B 17/00234 606/41 |
| 2012/0138660 A1* | 6/2012 | Shelton, IV | A61B 17/115 227/176.1 |
| 2012/0209288 A1* | 8/2012 | Robinson | A61B 17/07207 606/130 |
| 2013/0105552 A1* | 5/2013 | Weir | A61B 17/07207 227/180.1 |
| 2013/0206814 A1* | 8/2013 | Morgan | A61B 17/07207 227/176.1 |
| 2014/0332582 A1* | 11/2014 | Scirica | A61B 17/07207 227/180.1 |
| 2015/0053749 A1* | 2/2015 | Shelton, IV | A61B 17/068 227/181.1 |
| 2015/0316431 A1* | 11/2015 | Collins | A61B 90/98 606/219 |
| 2016/0066916 A1* | 3/2016 | Overmyer | A61B 17/105 227/176.1 |
| 2016/0100839 A1* | 4/2016 | Marczyk | A61B 17/07207 227/175.3 |

FOREIGN PATENT DOCUMENTS

| | | |
|---|---|---|
| WO | WO 98/37825 | 9/1998 |
| WO | WO 03/026511 | 4/2003 |
| WO | WO 2007/137304 | 11/2007 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15—1—Sire SHA-256 Secure Authenticator with 512-Bit User EEPROM"; IC-On-line, Electronic Component Manufacturers, pp. 1-2; Aug. 2013.

Detemple, P., "Microtechnology in Modern Health Care", *Med Device Technol*. 9(9):18-25 (1998).

Mouser Electronics, "Slide-In Mount Contacts" M60 p. 13-1562, Keystone Electronics, Astoria, NY (2013).

* cited by examiner

AUTHENTICATION SYSTEM FOR REUSABLE SURGICAL INSTRUMENTS

BACKGROUND

Technical Field

The present disclosure relates to surgical instruments having a reusable handle and a disposable end effector. More particularly, the present disclosure relates to an authentication assembly for use in a stapling instrument having a disposable loading unit.

Description of Related Art

Powered surgical instruments for use in endoscopic procedures are known. Typically, such instruments include a reusable handle assembly, and a disposable end effector sometimes referred to as single use loading unit or SULU. An adapter assembly connects the end effector to the handle assembly. In the case of a surgical stapler, the end effector includes a disposable cartridge or loading unit that is changed after each firing of the surgical stapler. To reduce costs and shorten procedure times, the handle assemblies are generally configured for use with a variety of reload assemblies of various configurations for use on tissue having different properties, e.g., thickness and density. For example, the different reload assemblies may have staples of different sizes and/or the staples may be arranged in different configurations. To ensure the handle assembly is programmed to operate with the attached reload assembly, some reload assemblies are provided with an integrated circuit, also known as a chip, that communicates with the handle assembly to identify the configuration of the reload assembly. This arrangement enables the configuration of the loading unit to be automatically conveyed to the handle assembly upon attachment of the loading unit to the adapter assembly, thereby eliminating user error or incompatibility that may be experienced when switching between reload assemblies with different configurations.

Surgical staplers are commonly used for stapling tissue within a body cavity where the end effector is likely to come in contact with fluids, e.g., blood, bile, and/or irrigation solutions. If the interconnections between the chip and the handle assembly are compromised, the chip could malfunction or data communications between the disposable loading unit and the handle assembly could be disrupted, rendering the surgical stapler unstable or inoperable.

A stapling instrument configured to increase the reliability of communications between the disposable loading unit and the handle assembly would be a welcome advance.

SUMMARY

In one aspect, the present disclosure is directed to an authentication system. In embodiments, the authentication system includes an authentication board assembly disposed on a loading unit configured to be secured to a surgical stapling device. The authentication board assembly includes a first circuit board having a proximal end and a distal end, a contact assembly fixed to the proximal end of the first circuit board and extending proximally therefrom, and a chip fixed to the first circuit board in operable communication with the contact assembly. The authentication system includes an adapter board assembly disposed on a surgical stapling device. The adapter board assembly includes a second circuit board having an upper surface and a lower surface, at least one contact fixed to the lower surface of the second circuit board, and a spring disposed on the upper surface of the second circuit board. The contact assembly of the authentication board is configured to engage the at least one contact of the adapter board assembly.

In some embodiments, the chip includes authentication data relating to the loading unit, such as, without limitation, cartridge size, staple arrangement, staple length, clamp-up distance, date of manufacture, expiration date, compatibility characteristics, unique identifier, and number of uses. In some embodiments, the chip includes encrypted data. In some embodiments, the chip authenticates the loading unit using an SHA algorithm. In some embodiments, the chip includes a 1-wire bidirectional serial communications interface.

In some embodiments, the adapter board includes a spring clip configured to retain the adapter board assembly to a surgical stapling device.

In some embodiments, the contact assembly of the authentication board assembly further includes a short contact arm having a first contact member orthogonally disposed and fixed to an upper portion of a proximal end thereof, a long contact arm having a second contact member orthogonally disposed and fixed to an upper portion of a proximal end thereof, and a solder tab orthogonally disposed and fixed to a lower portion of a distal end of at least one of the short contact arm or the long contact arm.

In another aspect, the present disclosure is directed to a surgical stapling device. The disclosed surgical stapling device includes a handle assembly, an adapter assembly extending distally from the handle assembly, and a loading unit operably connectable to a distal end of the adapter assembly. The adapter assembly includes an adapter circuit board disposed at a distal end of the adapter assembly and having an upper surface and a lower surface, at least one contact fixed to the lower surface of the second circuit board, and a spring disposed on the upper surface of the second circuit board. The loading unit includes an authentication circuit board disposed at a proximal end of the loading unit having a proximal end and a distal end, a contact assembly fixed to the proximal end of the authentication circuit board and extending proximally therefrom, and a chip fixed to the authentication circuit board in operable communication with the contact assembly. The contact assembly of the authentication circuit board engages the at least one contact of the adapter circuit board.

In some embodiments of the surgical stapling device, the chip includes authentication data relating to the loading unit such as, for example, cartridge size, staple arrangement, staple length, clamp-up distance, date of manufacture, expiration date, compatibility characteristics, unique identifier, and number of uses. In the chip includes encrypted data. In some embodiments of the surgical stapling device, the chip authenticates the loading unit using an SHA algorithm. In some embodiments of the surgical stapling device, the chip includes a 1-wire bidirectional serial communications interface. In some embodiments of the surgical stapling device, the chip is in operative communication with the handle assembly.

In some embodiments of the surgical stapling device, the adapter circuit board includes a spring clip configured to retain the adapter circuit board to the adapter assembly. In some embodiments of the surgical stapling device, the adapter assembly further includes an outer tube, and the spring of the adapter circuit board bears against this outer tube to bias the adapter circuit board assembly towards the authentication circuit board. In some embodiments of the surgical stapling device, a proximal end of the loading unit includes a contact support extending radially therefrom that includes a pair of cradles defined therein configured to receive the contact assembly of the authentication circuit board. In some embodiments of the surgical stapling device, the contact assembly of the authentication circuit board includes a short contact arm having a first contact member orthogonally disposed and fixed to an upper portion of a proximal end thereof, a long contact arm having a second contact member orthogonally disposed and fixed to an upper portion of a proximal end thereof, and a solder tab orthogonally disposed and fixed to a lower portion of a distal end of at least one of the short contact arm or the long contact arm.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely examples of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. As is common in the art, the term "proximal" refers to that part or component closer to the user or operator, i.e. surgeon or clinician, while the term "distal" refers to that part or component further away from the user. In addition, as used herein in the description and in the claims, terms referencing orientation, e.g., "top", "bottom", "upper", "lower", "left", "right", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions. Embodiments of the presently disclosed chip assembly will now be described in detail with reference to the drawings in which like reference numerals designate identical or corresponding elements in each of the several views. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Figure 1:
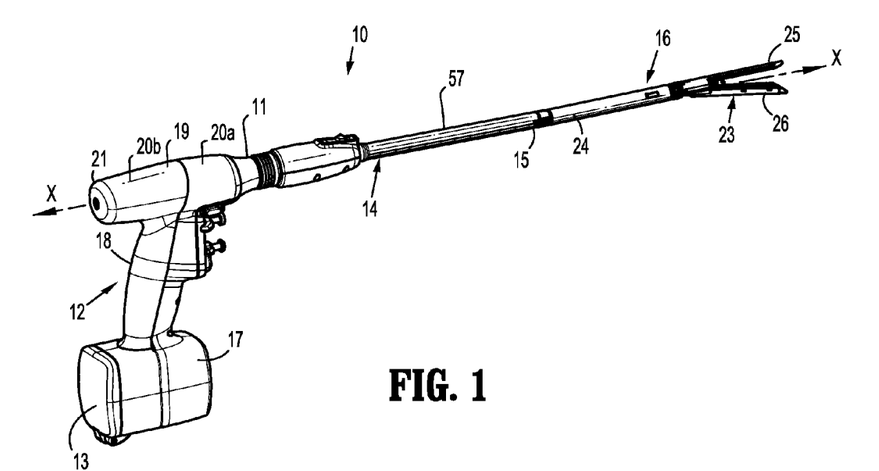
FIG. 1 is a perspective view of a surgical stapling device for use with a chip assembly according to embodiments of the present disclosure.
Figure 2:
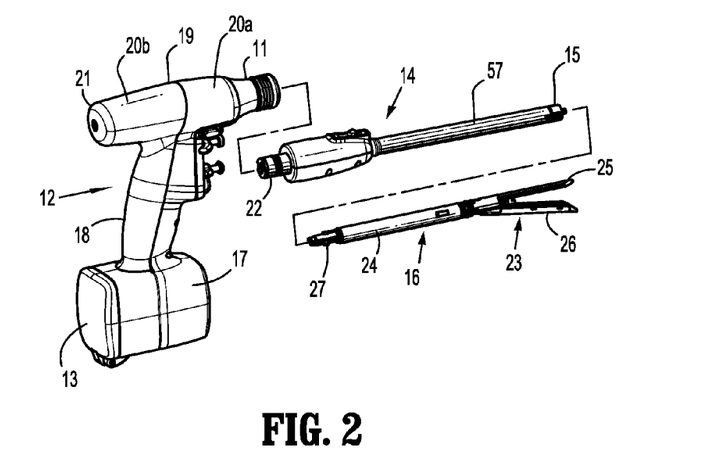
FIG. 2 is a perspective view of the surgical stapling device of FIG. 1 showing the handle assembly, adapter assembly, and loading unit in a separated configuration.

With reference initially to FIGS. 1 and 2, a surgical stapling instrument including an authentication system according to the present disclosure is shown generally as stapler 10. Stapler 10 includes a handle assembly 12, an adapter assembly 14 extending distally from handle assembly 12, and a loading unit 16 selectively secured to a distal end of adapter assembly 14. A detailed description of handle assembly 12, adapter assembly 14, and loading unit 16 is provided in commonly-owned U.S. Patent Appl. Publ. No. 2012/0089131, the contents of which is incorporated herein by reference in its entirety.

Handle assembly 12 includes a lower housing portion 17, an intermediate housing portion 18 extending from and/or supported on lower housing portion 17, and an upper housing portion 19 extending from and/or supported on intermediate housing portion 18. Intermediate housing portion 18 and upper housing portion 19 are separated into a distal half-section 20a that is integrally formed with, and extends from, the lower housing portion 17, and a proximal half-section 20b joined to distal half-section 20a by any suitable manner of attachment, such as without limitation, ultrasonic welding and/or a plurality of fasteners. When joined, distal and proximal half-sections 20a, 20b form a handle housing 21 defining a cavity therein which houses a circuit board that includes a controller (not shown), and a drive mechanism (not shown).

Lower housing portion 17 includes a door 13 pivotally connected thereto for accessing a cavity formed in lower housing portion 17 for retaining a battery (not shown) therein. It is contemplated that stapler 10 may be powered by any number of power sources, such as, for example and without limitation, a fuel cell, a power cord connected to an external power source, and so forth.

Adapter assembly 14 includes a drive coupler 22 at a proximal end thereof and coupled to a loading unit coupler 15 at a distal end thereof. Distal half-section 20a of upper housing portion 19 defines a nose or connecting portion 11 configured to operably receive drive coupler 22 of adapter assembly 14. Loading unit 16 includes an adapter coupler 27 configured to operably receive loading unit coupler 15 of adapter assembly 14.

Upper housing portion 19 of handle housing 21 encloses a drive mechanism (not shown) configured to drive shafts and/or gear components (not shown) in order to perform the various operations of stapler 10. In particular, the drive mechanism is configured to drive shafts and/or gear components in order to selectively move a tool assembly 23 of loading unit 16 relative to a proximal body portion 24 of loading unit 16, to rotate loading unit 16 about a longitudinal axis "X-X" (FIG. 1) relative to handle housing 21, to move an anvil assembly 25 relative to cartridge assembly 26 of loading unit 16, and/or to fire a stapling and cutting cartridge within cartridge assembly 26 of loading unit 16.

Figure 3:
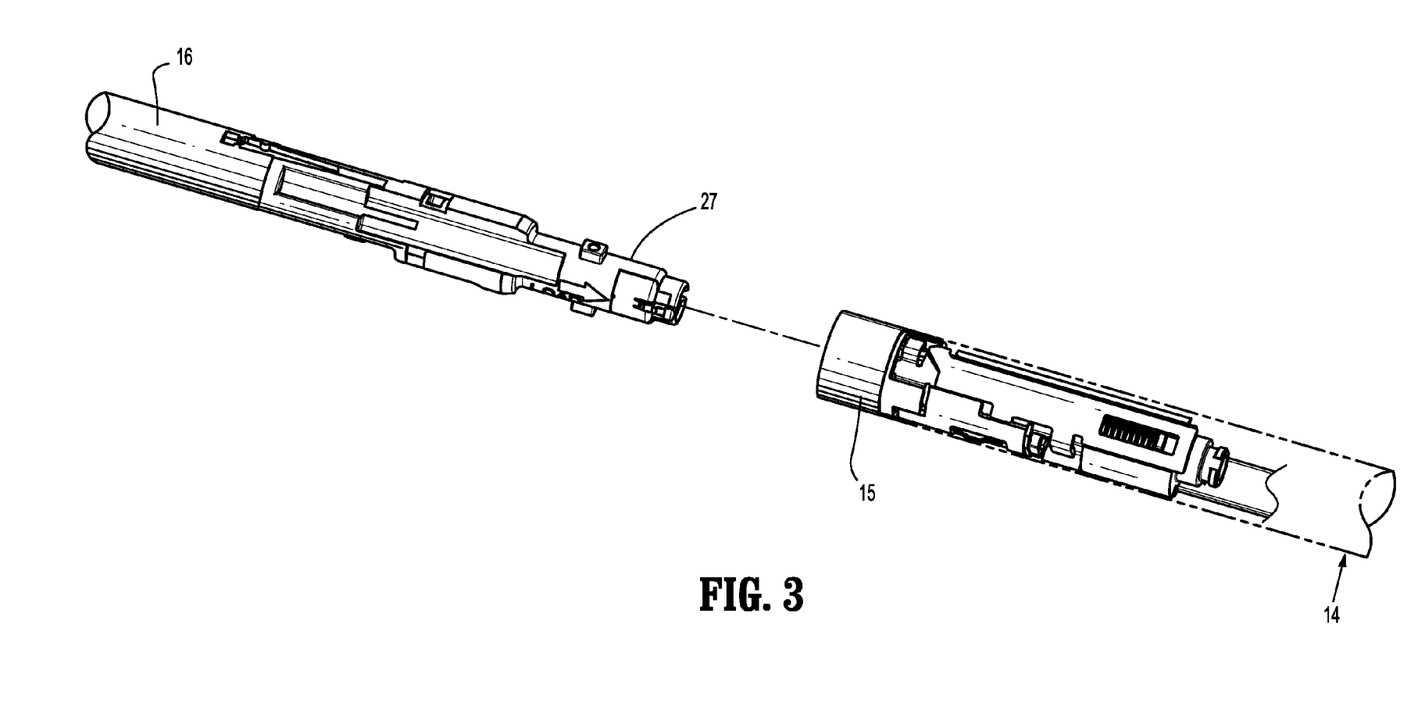
FIG. 3 is a view of a proximal end of a loading unit and a distal end of an adapter assembly of the surgical stapling device shown in FIG. 1.
Figures 4, 5:
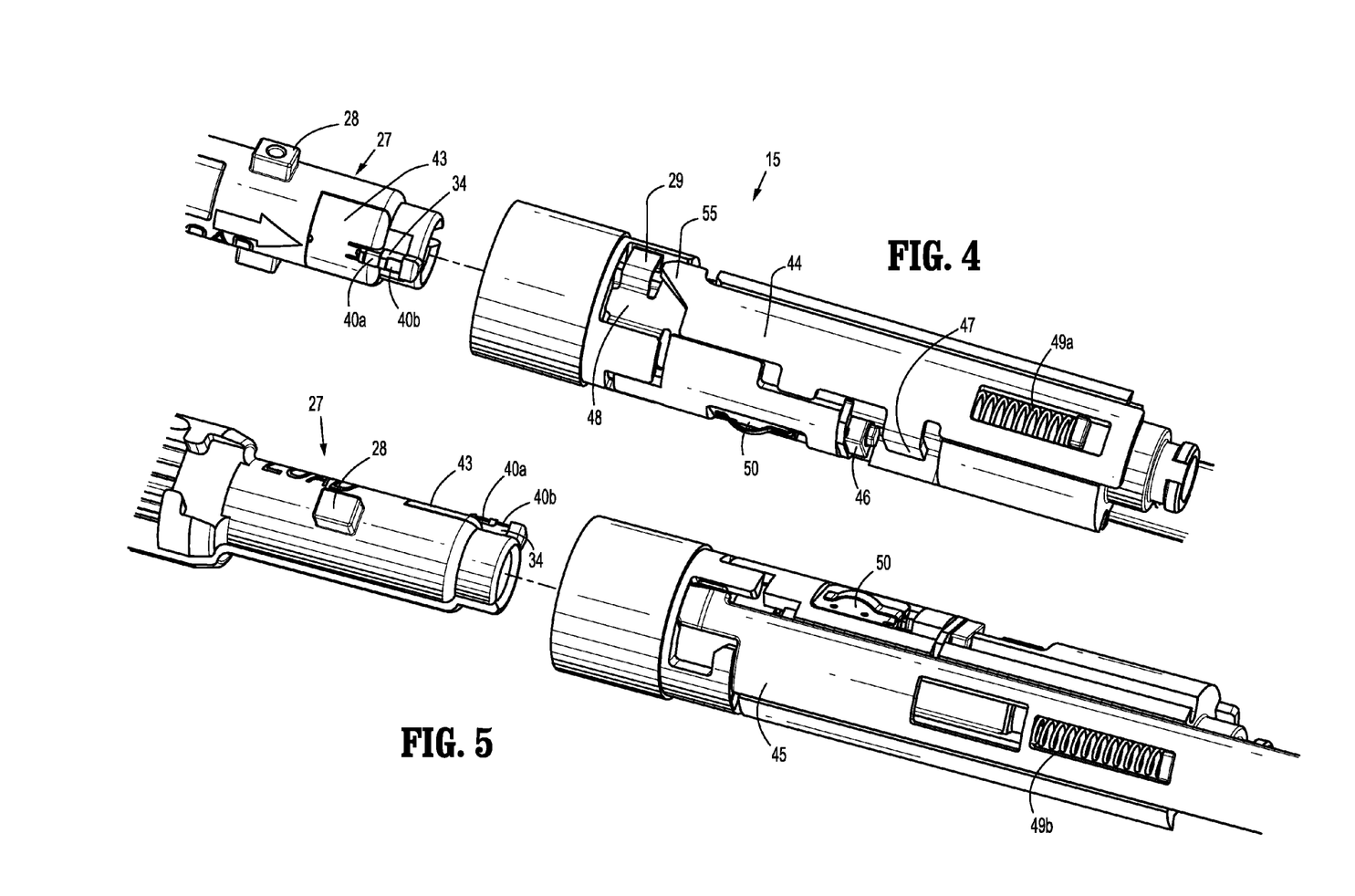
FIG. 4 is an enlarged view of the proximal end of the loading unit and the distal end of the adapter assembly shown in FIG. 3.
FIG. 5 is another enlarged view of the proximal end of the loading unit and the distal end of the adapter assembly shown in FIG. 3.
Figure 6:
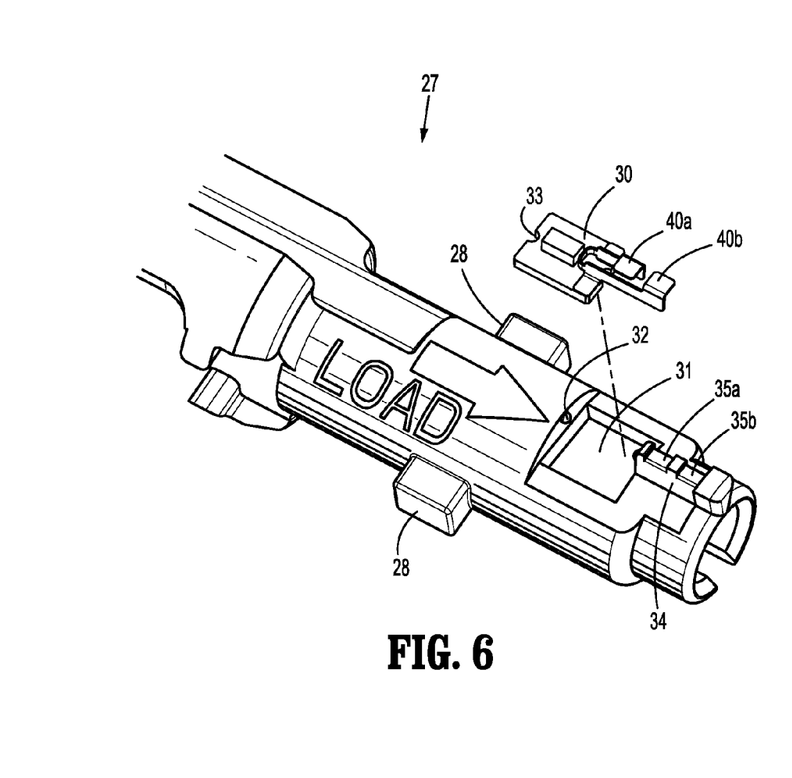
FIG. 6 is an enlarged, exploded view of the proximal end of the loading unit shown in FIG. 3 with the loading unit and authentication board separated.

With reference to FIGS. 3, 4, and 5, loading unit coupler 15 of adapter assembly 14 is configured to operably engage adapter coupler 27 of loading unit 16 via a push and twist or bayonet-type arrangement. Adapter coupler 27 includes one or more bayonet lugs 28 that are configured to mate with corresponding one or more bayonet channels 29 defined in a bayonet collar 48 provided by loading unit coupler 15 of adapter assembly 14. A short link member 44 and a load link member 45 are longitudinally disposed within adapter assembly 14 and are configured to translate longitudinally (e.g., distally and proximally) during operation of stapler 10. A cam 55 disposed at a distal end of short link member 44 is urged distally against a bayonet channel 29 by spring 49a. To engage loading unit 16 with adapter assembly 14, adapter coupler 27 of loading unit 16 is inserted into loading unit coupler 15 of adapter assembly 14 and rotated. In turn, bayonet collar 48 rotates cooperatively with adapter coupler 27. As bayonet collar 48 rotates, cam 55 rides off bayonet channel 29, causing short link member 44 to translate distally, which, in turn, causes a switch tab 47 formed in short link member 44 to actuate switch 46. Switch 46 is in operative electrical communication with the controller (not shown) and is configured to convey thereto the engagement status between loading unit 16 and adapter assembly 14.

Figure 11:
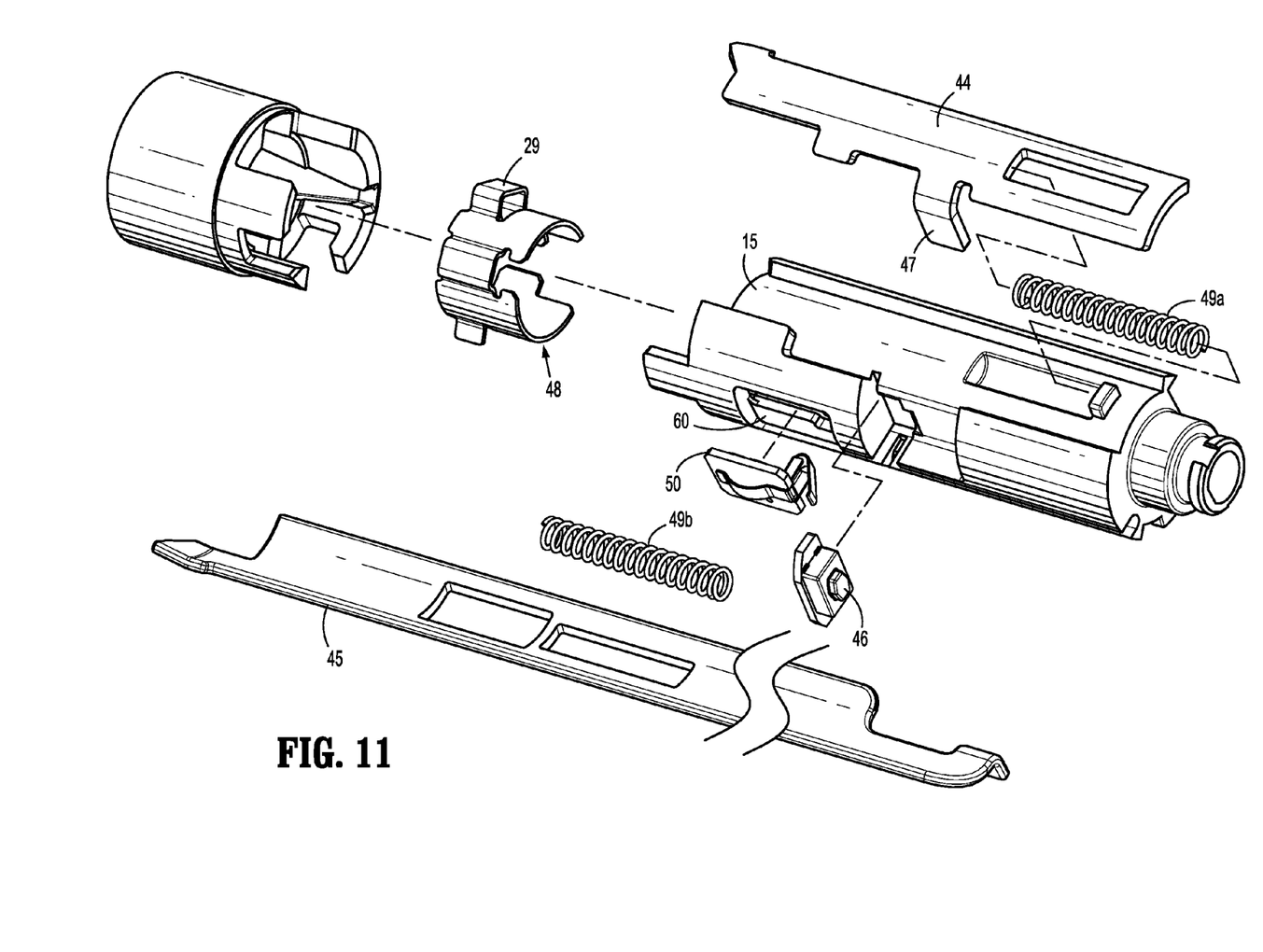
FIG. 11 is an enlarged, exploded view of the distal end of the adapter assembly shown in FIG. 3 with the adapter assembly and adapter board separated.
Figure 12:
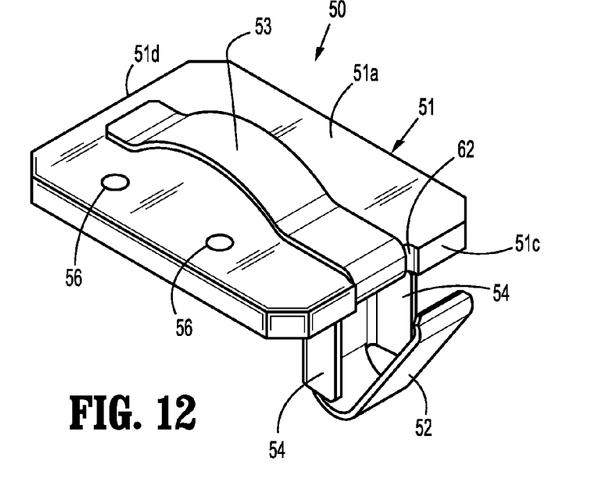
FIG. 12 is an enlarged view of the adapter board shown in FIG. 11.
Figure 13:
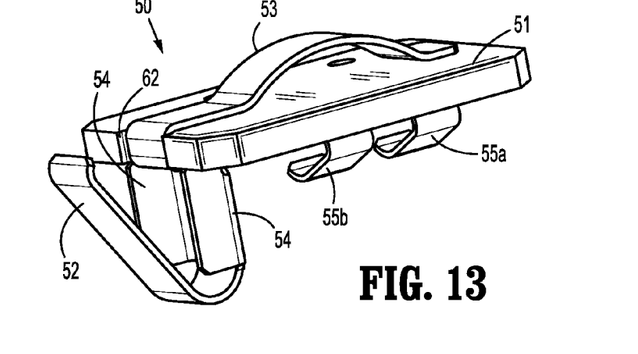
FIG. 13 is another enlarged view of the adapter board shown in FIG. 11.
Figure 14:
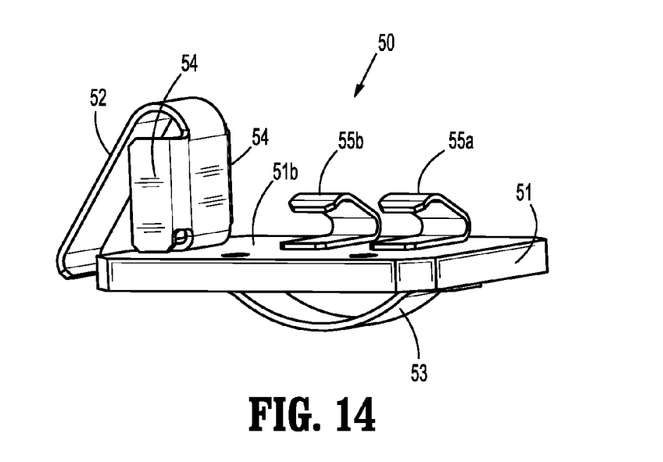
FIG. 14 is yet another enlarged view of the adapter board shown in FIG. 11.

Turning now to FIGS. 6-10, adapter coupler 27 includes an authentication board assembly 30 that is configured to be securely mounted within a recess 31 defined in adapter coupler 27. Authentication board assembly 30 is positioned within adapter coupler 27 such that when loading unit 16 is secured to adapter assembly 14, authentication board assembly 30 engages an adapter board assembly 50 mounted within loading unit coupler 15 (FIG. 11). In more detail, authentication board 30 includes a circuit board 37, a pair of contact members 40a, 40b (collectively, contact members 40) and a chip 36. Circuit board 37 defines a substantially planar elongated member configured to be securely received within recess 31 defined by adapter coupler 27. Chip 36 is in electrical communication with contact members 40. A distal end 37a of circuit board 37 supports chip 36, and a proximal end 37b of circuit board 37 supports contact members 40. Distal end 37a of circuit board 37 includes an alignment notch 33 defined therein that is configured to engage a corresponding alignment nub 32 provided at a distal end of recess 31 to ensure secure and accurate positioning of authentication board assembly 30 within adapter coupler 27.

Chip 36 includes any chip capable of storing the specifications of loading unit 16, such as, without limitation, cartridge size, staple arrangement, staple length, clamp-up distance, date of manufacture, expiration date, compatibility characteristics, a unique identifier (e.g., a serial number), and/or number of uses, and transmitting the specifications to handle assembly 12. In some embodiments, chip 36 includes an erasable programmable read only memory ("EPROM") chip. In this manner, the handle assembly 12 may adjust the firing forces, firing stroke, and/or other operational characteristics thereof in accordance with the specifications of loading unit 16 that are transmitted from chip 36. It is further envisioned that chip 36 may include write capabilities which allow handle assembly 12 to communicate to chip 36 that the associated loading unit 16 has been used, which can prevent reloading or reuse of an expended reload assembly, or any other unauthorized use.

In some embodiments, chip 36 includes a secure authentication chip, such as, without limitation, a DS28E15 Deep-Cover™ Secure Authenticator with 1-Wire SHA-256 and 512-Bit User EEPROM, manufactured by Maxim Integrated™ of San Jose, Calif. In these embodiments, the contents of chip 36, and the communications between chip 36 and handle assembly 12, are encrypted to prevent unauthorized access. In this manner, the use of low-quality counterfeit, re-manufactured, or "knock-off" loading units is effectively discouraged, which, in turn, reduces risk to patients by ensuring that only fresh, authentic loading units 16 are used during surgical procedures. In addition, the likelihood that medical facilities and/or surgeons may be exposed to liability for unwittingly using counterfeit loading units is greatly curtailed, thus reducing the overall costs to society for delivering medical services. In some embodiments, chip 36 utilizes a "1-wire" communications interface whereby a single signal conductor is employed, together with a ground conductor, for bidirectional serial communications between chip 36 and handle assembly 12.

Contact assembly 38 (FIGS. 9, 10) includes a short contact arm 41 and a long contact arm 42 joined by a contact base 59, and having a generally elongated u-shaped configuration. Short contact arm 41 includes a first contact member 40a orthogonally disposed and fixed to an upper portion of a proximal end thereof. Long contact arm 42 includes a second contact member 40b orthogonally disposed and fixed to an upper portion of a proximal end thereof. Short and long contact arms 41, 42 each include a solder tab 39 orthogonally disposed and fixed to a lower portion of a distal end thereof. Solder tabs 39 are electromechanically joined to a proximal end 37b of circuit board 37 by, e.g., soldering, electrically conductive adhesive, and/or other suitable technique.

Figure 7:
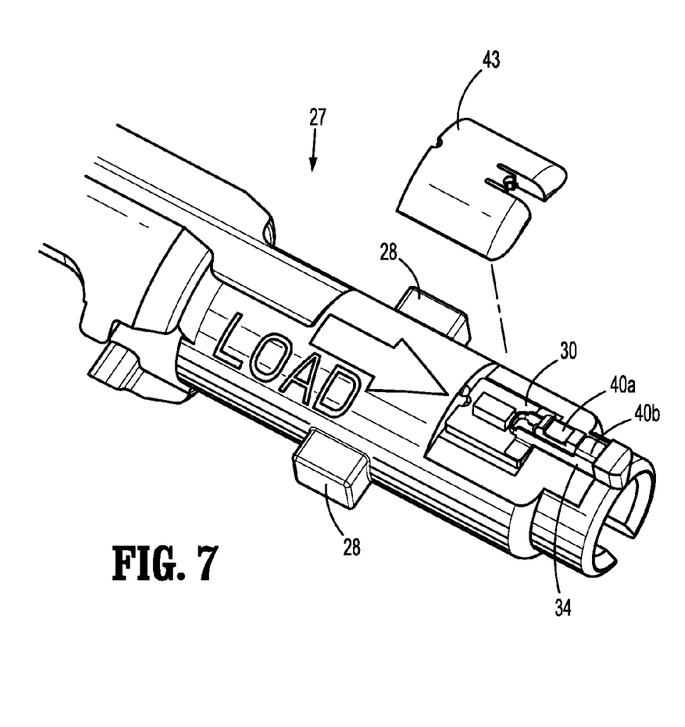
FIG. 7 is an enlarged, partially-exploded view of the proximal end of the loading unit shown in FIG. 3 with the authentication board cover separated from the loading unit.
Figure 8:
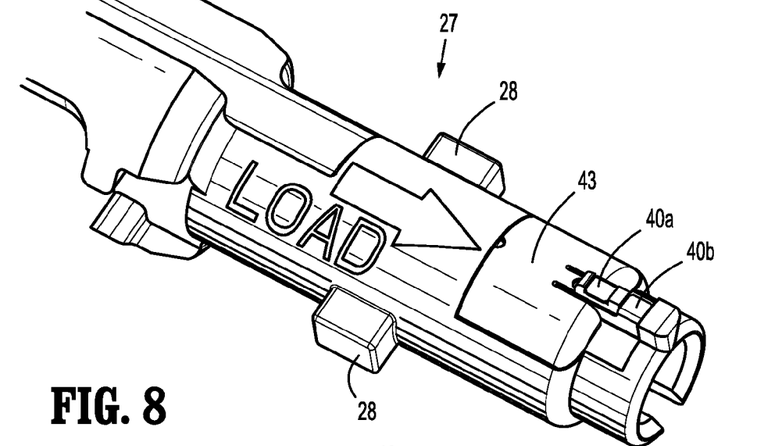
FIG. 8 is an enlarged view of the proximal end of the loading unit shown in FIG. 3.
Figure 9:
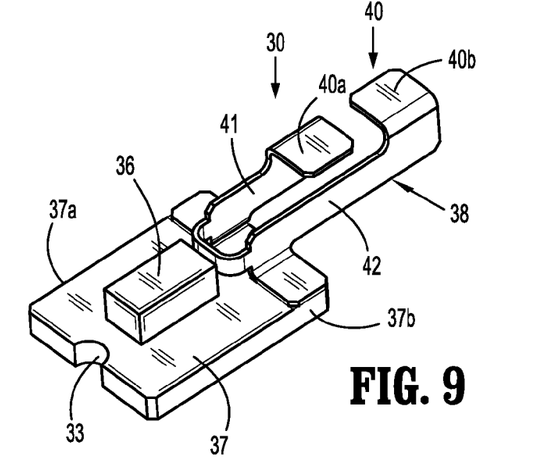
FIG. 9 is a perspective view of an authentication board assembly according to an embodiment of the present disclosure.
Figure 10:
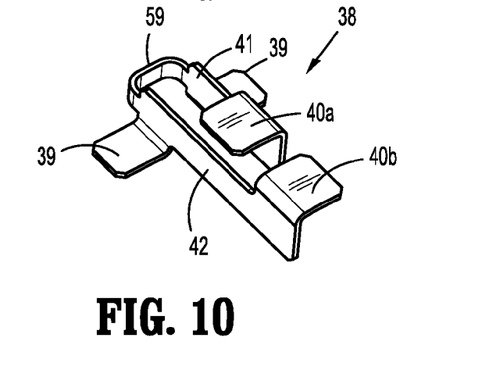
FIG. 10 is a perspective view of an authentication board contact.

Adapter coupler 27 includes a raised contact support 34 extending radially from a proximal end thereof and includes a pair of cradles 35a, 35b defined therein that are configured to receive first contact member 40a and second contact member 40b, respectively, when authentication board assembly 30 is positioned within recess 31 of adapter coupler 27. A cover 43 is configured to enclose and retain authentication board assembly 30 within recess 31 of adapter coupler 27 (FIGS. 7 and 8).

In some embodiments, short contact arm 41 and first contact member 40a are electrically insulated from long contact arm 42 and second contact member 40b by contact base 59. In these embodiments, each of short contact arm 41 and long contact arm 42 carries a separate circuit, e.g., short contact arm 41 carries signal and long contact arm 42 carries ground. In other embodiments, short contact arm 41 and first contact member 40a are electrically joined with long contact arm 42 and second contact member 40b. In these embodiments, short contact arm 41 and long contact arm 42 operate in a bifurcated or redundant mode to carry a signal circuit, while the ground circuit is carried through other electrically conductive components of loading unit 16, adapter unit 14, and/or handle assembly 12.

As mentioned above, authentication board assembly 30 is configured to engage adapter board assembly 50 mounted within loading unit coupler 15 when loading unit 16 is secured to adapter assembly 14. With reference now to FIGS. 11-14, loading unit coupler 15 includes an adapter board assembly 50 that is configured to be floatingly mounted within a pocket 60 defined in loading unit coupler 15. Adapter board assembly 50 is positioned within loading unit coupler 15 such that when loading unit 16 is secured to adapter assembly 14, adapter board assembly 50 engages authentication board assembly 30.

Adapter board assembly 50 includes a circuit board 51 having a pair of contact members 55a, 55b (collectively, contact members 55) fixed thereto and in operable communication with handle assembly 12. In the illustrated embodiment, contact members 55a, 55b are arranged for effective engagement in a transverse direction, e.g., transverse to the longitudinal axis "X-X" of stapler 10, to accommodate the rotational coupling of loading unit 16 and adapter assembly 14 as described herein.

Circuit board 51 includes an upper surface 51a, a lower surface 51b, a proximal end 51c, and a distal end 51d. Circuit board 51 defines a substantially planar elongated member configured to be resiliently or floatingly received within pocket 60 defined by loading unit coupler 15. A spring clip 52 is fixed to a proximal end 51c of circuit board 51 and is configured to support adapter board assembly 50 within pocket 60. Spring clip 52 includes a pair of spring supports 54 having a wing-like configuration that are configured prevent spring clip 52 from over-extension and to provide stiffness thereto. Adapter board assembly 50 includes a spring 53 having a broad, curvate u-shaped profile disposed on an upper surface 51a of circuit board 51. In some embodiments, spring clip 52 and spring 53 may be integrally formed. Spring clip 52 and/or spring 53 may be positively aligned and/or supported by a notch 62 defined in proximal end 51c of circuit board 51. Circuit board 51 includes one or more through holes 56 defined therein that may be utilized to form a conductive pathway between upper surface 51a and lower surface 51b of circuit board 51.

Figure 15:
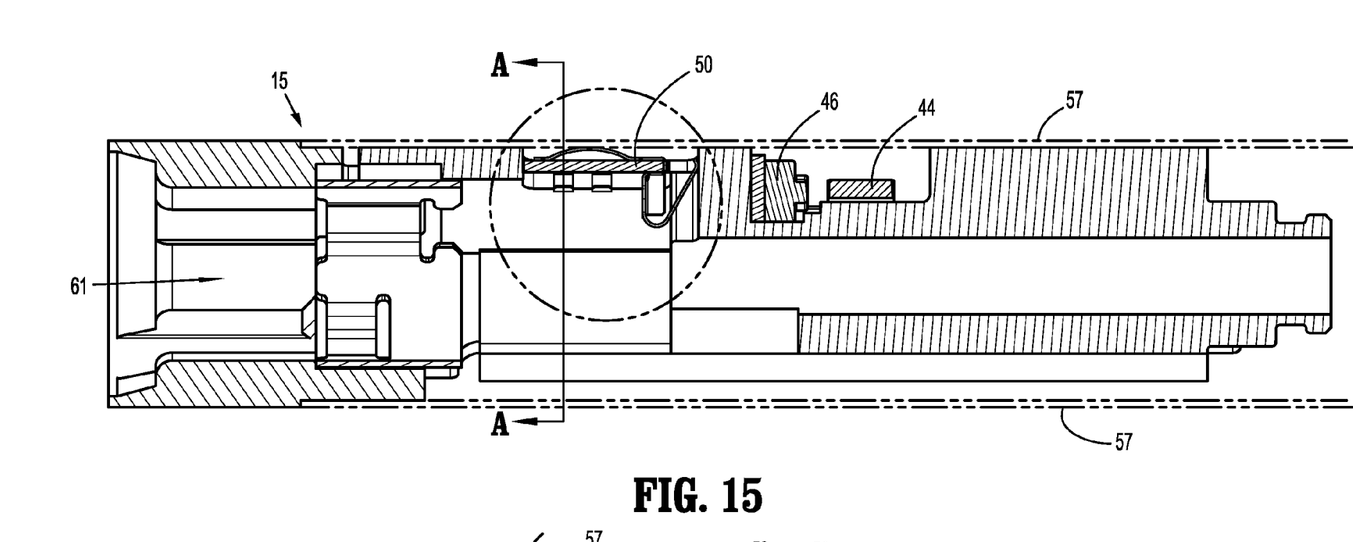
FIG. 15 is a cross-sectional, side view of the adapter assembly shown in FIG. 3 showing the adapter assembly separated from the loading unit.
Figure 16:
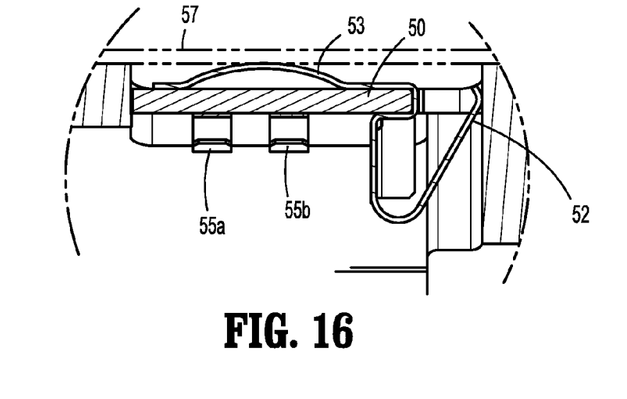
FIG. 16 is an enlarged view of the indicated area shown in FIG. 15 showing the adapter board separated from the authentication board.
Figure 17:
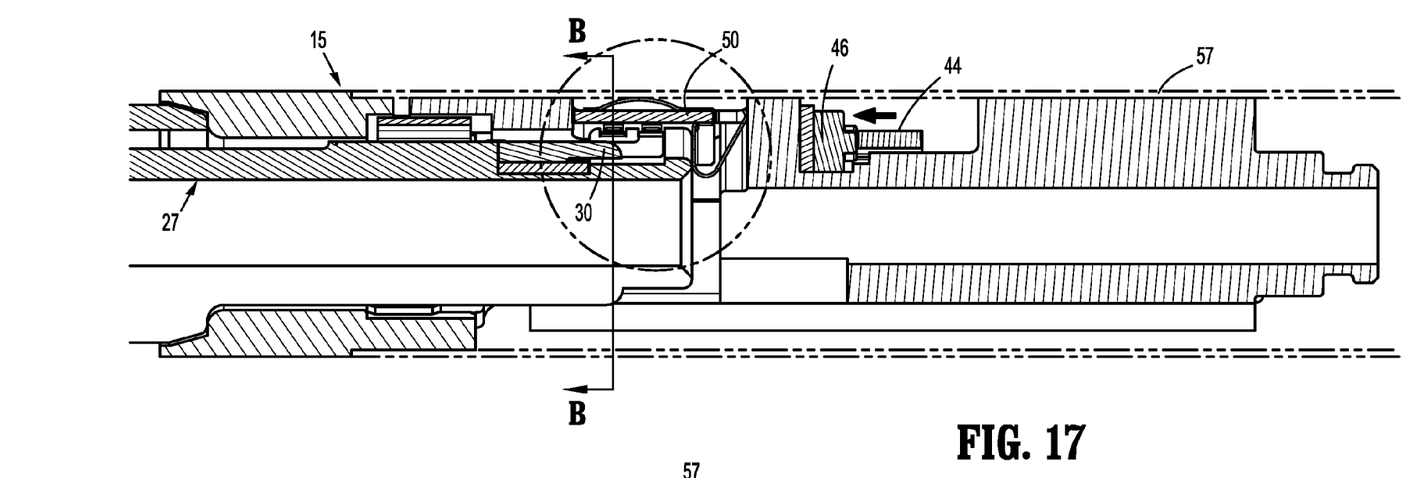
FIG. 17 is a cross-sectional, side view of the adapter assembly shown in FIG. 3 showing the adapter assembly engaged with the loading unit.
Figure 18:
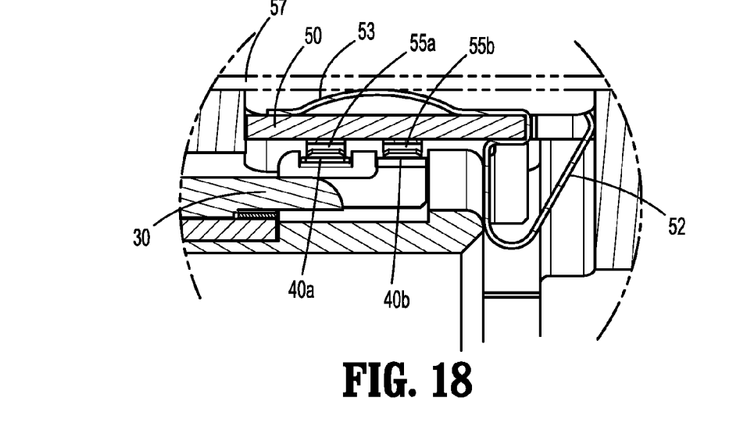
FIG. 18 is an enlarged view of the indicated area shown in FIG. 17 showing the adapter board engaged with the authentication board.

When adapter board assembly 50 is mounted within pocket 60, spring 53 bears against outer tube 57 of adapter assembly 14 (FIGS. 15, 16). In use, adapter board assembly 50 is spring-biased towards authentication board assembly 30 by spring 53 and by side spring clip 52 such that, upon joining loading unit 16 and adapter assembly 14, any manufacturing tolerances between loading unit 16 and adapter assembly 14 are compensated for by engagement of the floating spring mount of adapter board assembly 50 within pocket 60. In this manner, a reliable connection between contact members 55 of adapter board assembly 50 and contact members 40 of authentication board assembly 30 is consistently achieved, thus providing a robust communication link between chip 36 and handle assembly 12. In embodiments, contact assembly 38, contacts 40, and/or contacts 55 are formed at least in part from electrically conductive material, such as, without limitation, beryllium copper.

Figure 19:
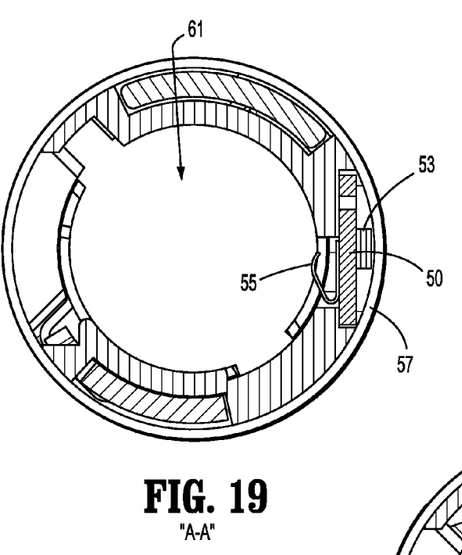
FIG. 19 is a cross-sectional, axial view of the adapter assembly shown in FIG. 3 showing the adapter assembly separated from the loading unit.
Figure 20:
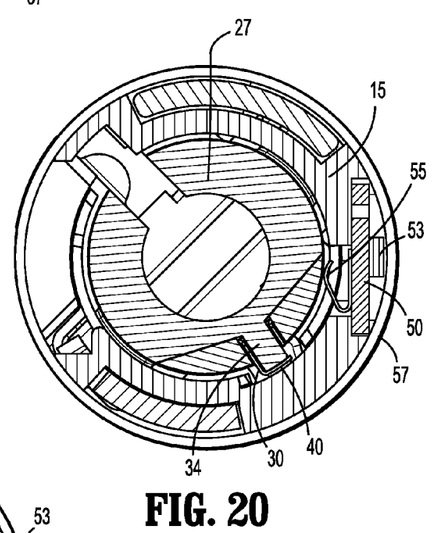
FIG. 20 is a cross-sectional, axial view of the adapter assembly shown in FIG. 3 showing the loading unit inserted into the adapter assembly.
Figure 21:
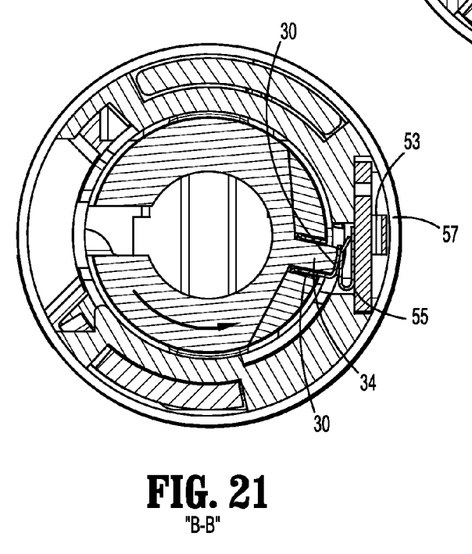
FIG. 21 is a cross-sectional, axial view of the adapter assembly shown in FIG. 3 showing the loading unit engaged with the adapter assembly.

Turning now to FIGS. 15-21, the interaction between adapter board assembly 50 and authentication board assembly 30 is shown. As seen in FIGS. 15, 16, and 19, adapter board assembly 50 is retained within loading unit adapter 15 by spring clip 52. Spring 53 bears against outer tube 57 to bias adapter board assembly 50 inwardly towards bore 61, such that contact members 55 extend into bore 61. As adapter coupler 27 is inserted fully into bore 61 of loading unit adapter 15, the initial rotational orientation of adapter coupler 27 and loading unit coupler 15 is such that contact members 40 of authentication board assembly 30 and contact members 55 of adapter board assembly 50 are roughly 45° apart (FIG. 20). As loading unit 16 is rotated with respect to adapter assembly 14, contact members 40 of authentication board assembly 30 are brought into engagement with contact members 55 of adapter board assembly 50. Advantageously, contact support 34 of adapter coupler 27 of loading unit 16 provides radial support to contact members 40 as they engage mating contact members 55 of adapter board assembly 50. In addition, spring 53 bears against outer tube 57 which enables adapter board assembly 50 to float with respect to authentication board assembly 30 and loading unit coupler 15, thereby compensating for manufacturing variations between the various components and providing a reliable connection between authentication board assembly 30 and adapter board assembly 50.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An authentication system, comprising:
  an authentication board assembly disposed on a loading unit configured to be secured to a surgical stapling device, including:
    a first circuit board having a proximal end and a distal end;
    a contact assembly fixed to the proximal end of the first circuit board and extending proximally therefrom; and
    a chip fixed to the first circuit board in operable communication with the contact assembly; and
  an adapter board assembly disposed on a surgical stapling device, including:
    a second circuit board having an upper surface and a lower surface;
    at least one contact fixed to the lower surface of the second circuit board; and
    a spring disposed on the upper surface of the second circuit board;
  wherein the contact assembly of the authentication board assembly is configured to engage the at least one contact of the adapter board assembly, and wherein the contact assembly of the authentication board assembly further comprises:
  a short contact arm having a first contact member orthogonally disposed and fixed to an upper portion of a proximal end of the short contact arm;
  a long contact arm having a second contact member orthogonally disposed and fixed to an upper portion of a proximal end of the long contact arm; and
  a solder tab orthogonally disposed and fixed to a lower portion of a distal end of at least one of the short contact arm or the long contact arm.

2. The authentication system in accordance with claim 1, wherein the chip includes authentication data relating to the loading unit selected from the group consisting of cartridge size, staple arrangement, staple length, clamp-up distance, date of manufacture, expiration date, compatibility characteristics, unique identifier, and number of uses.

3. The authentication system in accordance with claim 1, wherein the chip includes encrypted data.

4. The authentication system in accordance with claim 1, wherein the chip authenticates the loading unit using an SHA algorithm.

5. The authentication system in accordance with claim 1, wherein the chip includes a 1-wire bidirectional serial communications interface.

6. The authentication system in accordance with claim 1, wherein the adapter board assembly further includes a spring clip configured to retain the second circuit board to the adapter board assembly.

7. A surgical stapling device, comprising:
  a handle assembly;
  an adapter board assembly extending distally from the handle assembly and including:
    an adapter circuit board disposed at a distal end of the adapter assembly, the adapter circuit board having an upper surface and a lower surface;
    at least one contact fixed to the lower surface of the adapter circuit board; and
    a spring disposed on the upper surface of the adapter circuit board;
  a loading unit operably connectable to a distal end of the adapter board assembly and including:
    an authentication board assembly disposed at a proximal end of the loading unit having a proximal end and a distal end;
    a contact assembly fixed to the proximal end of the authentication board assembly and extending proximally therefrom; and
    a chip fixed to the authentication board assembly in operable communication with the contact assembly,
  wherein the contact assembly of the authentication board assembly engages the at least one contact of the adapter circuit board, and
  wherein the adapter circuit board further includes a spring clip configured to retain the adapter circuit board to the adapter board assembly.

8. The surgical stapling device in accordance with claim 7, wherein the chip includes authentication data relating to the loading unit selected from the group consisting of cartridge size, staple arrangement, staple length, clamp-up distance, date of manufacture, expiration date, compatibility characteristics, unique identifier, and number of uses.

9. The surgical stapling device in accordance with claim 7, wherein the chip includes encrypted data.

10. The surgical stapling device in accordance with claim 7, wherein the chip authenticates the loading unit using an SHA algorithm.

11. The surgical stapling device in accordance with claim 7, wherein the chip includes a 1-wire bidirectional serial communications interface.

12. The surgical stapling device in accordance with claim 7, wherein the chip is in operative communication with the handle assembly.

13. The surgical stapling device in accordance with claim 7, wherein the adapter board assembly further includes an outer tube; and
  the spring of the adapter circuit board bears against the outer tube to bias the adapter circuit board assembly towards the authentication board assembly.

14. The surgical stapling device in accordance with claim 7, wherein a proximal end of the loading unit includes a contact support extending radially therefrom, the contact support including a pair of cradles defined therein configured to receive the contact assembly of the authentication board assembly.

15. The surgical stapling device in accordance with claim 7, wherein the contact assembly of the authentication board assembly further comprises:
  a short contact arm having a first contact member orthogonally disposed and fixed to an upper portion of a proximal end of the short contact arm;
  a long contact arm having a second contact member orthogonally disposed and fixed to an upper portion of a proximal end of the long contact arm; and
  a solder tab orthogonally disposed and fixed to a lower portion of a distal end of at least one of the short contact arm or the long contact arm.

16. An authentication system, comprising:
  an authentication board assembly disposed on a loading unit configured to be secured to a surgical stapling device, the authentication board assembly including:
    a first circuit board having a proximal end portion and a distal end portion;
    a contact assembly fixed to the proximal end portion of the first circuit board and extending proximally therefrom; and
    a chip fixed to the first circuit board in operable communication with the contact assembly; and
  an adapter board assembly disposed on a surgical stapling device, including:
    a second circuit board having an upper surface and a lower surface;
    at least one contact fixed to the lower surface of the second circuit board; and
    a spring disposed on the upper surface of the second circuit board,
      wherein the contact assembly of the authentication board assembly is configured to engage the at least one contact of the adapter board assembly, and wherein the adapter board assembly further includes a spring clip configured to retain the second circuit board to the adapter board assembly.

17. A surgical stapling device, comprising:
  a handle assembly;
  an adapter board assembly extending distally from the handle assembly and including:
    an adapter circuit board disposed at a distal end of the adapter assembly, the adapter circuit board having an upper surface and a lower surface;

at least one contact fixed to the lower surface of the adapter circuit board; and a spring disposed on the upper surface of the adapter circuit board;

a loading unit operably connectable to a distal end portion of the adapter board assembly and including:

an authentication board assembly disposed at a proximal end portion of the loading unit and having a proximal end portion and a distal end portion;

a contact assembly fixed to the proximal end portion of the authentication board assembly and extending proximally therefrom; and a chip fixed to the authentication board assembly in operable communication with the contact assembly, wherein the contact assembly of the authentication board assembly engages the at least one contact of the adapter circuit board, and wherein the contact assembly of the authentication board assembly includes:

a short contact arm having a first contact member orthogonally disposed and fixed to an upper portion of a proximal end portion of the short contact arm;

a long contact arm having a second contact member orthogonally disposed and fixed to an upper portion of a proximal end portion of the long contact arm; and a solder tab orthogonally disposed and fixed to a lower portion of a distal end portion of at least one of the short contact arm or the long contact arm.

* * * * *